(12) United States Patent
Tsai et al.

(10) Patent No.: US 8,741,619 B1
(45) Date of Patent: Jun. 3, 2014

(54) METHOD FOR PURIFYING PROTEIN AQUEOUS

(71) Applicant: Chung Yuan Christian University, Zhongli (TW)

(72) Inventors: Tsung-Yen Tsai, Pingzhen (TW); Shih-Sin Huang, Pingzhen (TW); Chao-Chen Hsu, Zhongli (TW)

(73) Assignee: Chung Yuan Christian University, Zhongli, Taoyuan County (TW)

( * ) Notice: Subject to any disclaimer, the term of this patent is extended or adjusted under 35 U.S.C. 154(b) by 0 days.

(21) Appl. No.: 13/757,335

(22) Filed: Feb. 1, 2013

(51) Int. Cl.
*C12N 9/36* (2006.01)
*C12P 7/54* (2006.01)

(52) U.S. Cl.
USPC .......................................... 435/206; 435/140

(58) Field of Classification Search
None
See application file for complete search history.

(56) References Cited

U.S. PATENT DOCUMENTS 7,611,812 B2 * 11/2009 Michel et al. .............. 430/108.2

OTHER PUBLICATIONS

Iyi et al "Decarbonation of MgAl-LDHs (layered double hydroxides) using acetate-buffer/NaCl mixed solutions" Journal of Colloid and Interface Science 322 (2008) 237-245.*

Lemos et al. "Cycloaddtion reactions of nitrosalkene, azoalkenes and nitrile oxides by hydotalcite" AEKIVOC 2010 (v) 170-182.*

Ma et al. "Exfoliating layered double hydroxides in formamide: a method to obtain positively charged nanosheets" J. Nater. Chem. (2006) 16: 3809-3813.*

Ralla et al. "Adsorption and separation of proteins by synthetic hydrotalcite" Colloids and Surfaces B: Biointerfaces 87 (2011) 217-225.*

Ralla et al. "Adsorption and separation of proteins by smectic clay mineral" Bioprocess Biosyst Eng (2011) 33:847-861.*

Manohara et al. "Reversible hydration and aqueous exfoliation of the acetate-intercalated layered double hydroxide of Ni and Al: Observation of an ordered interstratified phase" Journal of Solid State Chemistry (2012) 196 356-361.*

* cited by examiner

*Primary Examiner* — Suzanne M Noakes
*Assistant Examiner* — Gerard Lacourciere
(74) *Attorney, Agent, or Firm* — Muncy, Geissler, Olds & Lowe, P.C.

(57) ABSTRACT

A method for purifying protein aqueous is provided. A protein aqueous is first provided. An absorption material is mixed into the protein aqueous to form a first mixture. The first mixture is separated into a solid-liquid two phases solution by a first separation process. A buffer solution is added into the solid phase from the solid-liquid two phases solution which has a target protein therein to form a second mixture. Then, a second separation process is performed to separate the second mixture to obtain a purified protein aqueous.

9 Claims, 6 Drawing Sheets

METHOD FOR PURIFYING PROTEIN AQUEOUS

FIELD OF THE INVENTION

The present invention relates to protein purification, and in particular to an adsorption material is formed by an inorganic layered material to adsorb the protein to obtain a purified protein from the protein mixture.

BACKGROUND OF THE INVENTION

There are many protein purification method has been disclosed, such as shown in U.S. Pat. No. 5,278,284, issued in 1994 to Lusk et al, entitled "Protein Purification Method", U.S. Pat. No. 6,036,861, issued in 2000 to Flickinger et al, entitled "Protein adsorption by very dense porous zirconium oxide particles in expanded beds", U.S. Pat. No. 5,837,826, issued in 1998 to Flickinger et al, entitled "Protein adsorption by very dense porous zirconium oxide particles in expanded beds", U.S. Pat. No. 7,026,453, issued in 2006 to Haj-Ahmad, entitled "Method of protein purification", and Taiwan Patent No. 365,540, issued in 1999, to Adames Omar et al, entitled "A method for the removal of viruses from protein solutions by adsorption using solid phase suspension particles". Taiwan Patent No. 365,540 disclosed that adsorbent is selected from the group silicone, Zirconium oxide particles, diatomaceous and Silicon carbon compounds, and subsequently the solid phase is separated from the liquid phase by extraction to obtain the protein purification.

In addition, as shown in U.S. Pat. No. 6,339,142, issued in 2002 to Basey et al, entitled "Protein Purification", or in Taiwan Patent No. 128021, issued in 1990 to David Naveh, entitled "Method of Purifying Protein", or in Taiwan Publication No 201117883, published on 2011 to Chem, Ming Kai, entitled "Method For Protein Purification". Taiwan Publication No. 201117883 disclosed that the protein purification is performed by using an ion exchange resin and adjusting pH value of the buffer solution according to the different isoelectric point (PI) protein aqueous to achieve the effect of the protein purification.

In addition, as shown in Taiwan Patent No. 169,356, issued in 1991 to Staples et al, entitled "Process For Purifying a Protein" which disclosed a process for the purification of proteins from solutions containing contaminants of similar net charge and molecular weight is provided, comprising contacting a solution containing the desired protein with an immobilized metal affinity chromatography resin in a buffer containing a low concentration of a weak ligand for the chelant of the resin. In addition, as shown in Taiwan Publication No. 200300173, published on 2003 to Minoshima, entitled "Process For Producing Concentrated/Purified Protein Using Clay Mineral Composition" which disclosed a method for isolating a protein characterized in that a protein adsorbed on a clay mineral-containing composition is isolated using at least one member selected from the group consisting of fatty acid esters whose fatty acid residue has a carbon atom number of not more than 30. In Minoshima, utilized the ion exchange, molecular sieving effect, gel filtration chromatography or gel filtration chromatography with ampholine to purify the protein. Generally, the typical analysis method is isoelectric focusing (IEF). For separating, concentrating and purifying the crude protein aqueous, the crude protein aqueous is subjected to the desalination treatment and concentration treatment. Thus, the purification of the protein aqueous is quite complex and requires highly cost for the industrial scale, and the technical problems is also involved.

Minoshima also disclosed that a protein is adsorbed on a clay mineral and there have been known techniques for separating the protein from the clay mineral in which the protein adsorbed on the clay mineral is isolated through the use of an eluent having a different pH value or an ionic strength, but these techniques are accompanied with an abrupt change of pH or ionic strength, which may cause various changes in the higher-order structure of the protein strictly involved in the functionality thereof.

In addition, Chern, Ming Kai disclosed that ion exchange chromatography can apply for protein purification. In present technology, the ion exchange chromatography utilizes a sample with the protein which is loaded into a column with ion exchanger, and the charged groups on the protein and immobilized group of the ion exchange agent are interacted, such that the protein is absorbed on the ion exchange agent in the column, the above method can be called equilibrium model.

Next, the salt solution with increasing gradient concentration is imported in the same direction as sample with the protein. Thus, the protein with the degree of interaction which is different from the ion exchange agent that will be eluted sequentially in different salt concentrations, in which based on the prior art of ion exchange chromatography lacks of specific affinity. Thus, when ion exchange chromatography is used to purify a specific target protein, the target protein is to be separated from the wash solution by combined with other purification process, such as affinity chromatography. Thus, the purification process requires genetic engineering or the preparation of specific antibodies, and the cost of the purification would be increased.

Furthermore, in the field of analytical chemistry, for the separation of the inorganic species which develops a kind of reverse elution method, where it is inverted by simple elution flow direction of the sample loading to reduce the peak dispersion effect, and the problem of the irreversibility of the sample ions ion exchange (irreversible ion exchange) can be avoided, and the dip peak can also be reduced. Specifically, the sample is imported in the opposite direction to the direction of the elution, and is compressed to form a compact band by the initial stage of elution of the sample ions, such that the band broadening of the concentrator column will be minimized. Because the treating direction will influence the effect of separation, it is not only a balanced the interaction, and non-balanced interaction can also play an important role in the aforementioned method.

However, for comparing with the inorganic ions, the protein molecules are consisted by a plurality of amino acid molecules. According to the currently protein purification, the problems of the peak dispersion still exist. The fraction is separated from the salt concentration range of elution gradient which is further purified to obtain more protein with homogeneity. Therefore, the conventional prior art still lacks of disclosing a method for separating the protein with high homogeneity.

SUMMARY OF THE INVENTION

The major objective of the present invention is to provide a method for purifying the protein aqueous. The purifying method utilizes an adsorption material which is formed by an inorganic layered material to mix with the protein aqueous to purify the protein aqueous, and thus the purified protein aqueous can be obtained after separating process.

Another objective of the present invention is to utilize the adsorption material with surface charges to absorb the target protein on the adsorption material. Then, a buffer solution is added into the adsorption material with the target protein to separate the protein from the adsorption material. Thus, the purified protein can be obtained.

According to above objectives, the present invention provides a method for forming an adsorption material. The method includes an inorganic layered material is provided. Then, an organic solvent is added into inorganic layered material to swell the inorganic layered material. Next, an acetic acid solution is mixed with the swelled inorganic layered material to form a mixture. Then, a cleaning process with a cleaning solvent to clean the mixture. Next, a separating process is performed to separate the cleaned mixture to collect the plurality of solid precipitates. Finally, the plurality of solid precipitates is dried to obtain the adsorption material.

In an embodiment, the inorganic layered material is selected from the group consisting of layered double hydroxide and hydrotacite.

In an embodiment, the layered double hydroxides is Li—Al layered double hydroxide.

In an embodiment, the proportion of adding the inorganic layered material and the organic solvent is 1:5.

In an embodiment, the organic solvent is selected from the group consisting of formamide and dimethylformamide (DMF).

In an embodiment, the cleaning solvent is alcohol or acetone.

In an embodiment, the separating process is centrifuge separating process.

In an embodiment, the drying process is selected from the group consisting of heating process, extracting and concentrating process, and freeze-drying process.

In addition, the present invention also utilizes the adsorption material to absorb the target protein from the protein aqueous to obtain the purified protein. The purification method includes a protein aqueous which is provided. The adsorption material is added into the protein aqueous to form a first mixture. A first separating process is performed to separate the first mixture into a solid-liquid two phases solution. A buffer solution is added into a solid phase of the solid-liquid two phases solution to form a second mixture. Finally, a second separating process is performed to separate the second mixture to obtain the purified protein aqueous.

In an embodiment, the protein aqueous includes Bovine Serum Albumin (BSA) and Lysozyne (LYZ).

In an embodiment, the adsorption material is an acetified inorganic layered material.

In an embodiment, the buffer solution is an ion exchange solution.

In an embodiment, the first separating process and the second separating process is centrifuge separating process.

BRIEF DESCRIPTION OF THE DRAWINGS

The present invention will be apparent to those skilled in the art by reading the following description of a preferred embodiment thereof with reference to the drawings, in which.

DETAILED DESCRIPTION OF THE PREFERRED EMBODIMENT

The present invention is to disclose a purifying method for the protein. The method utilizes an adsorption material which is made of an inorganic layered material, and is mixed with the protein aqueous to purify the protein aqueous. The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
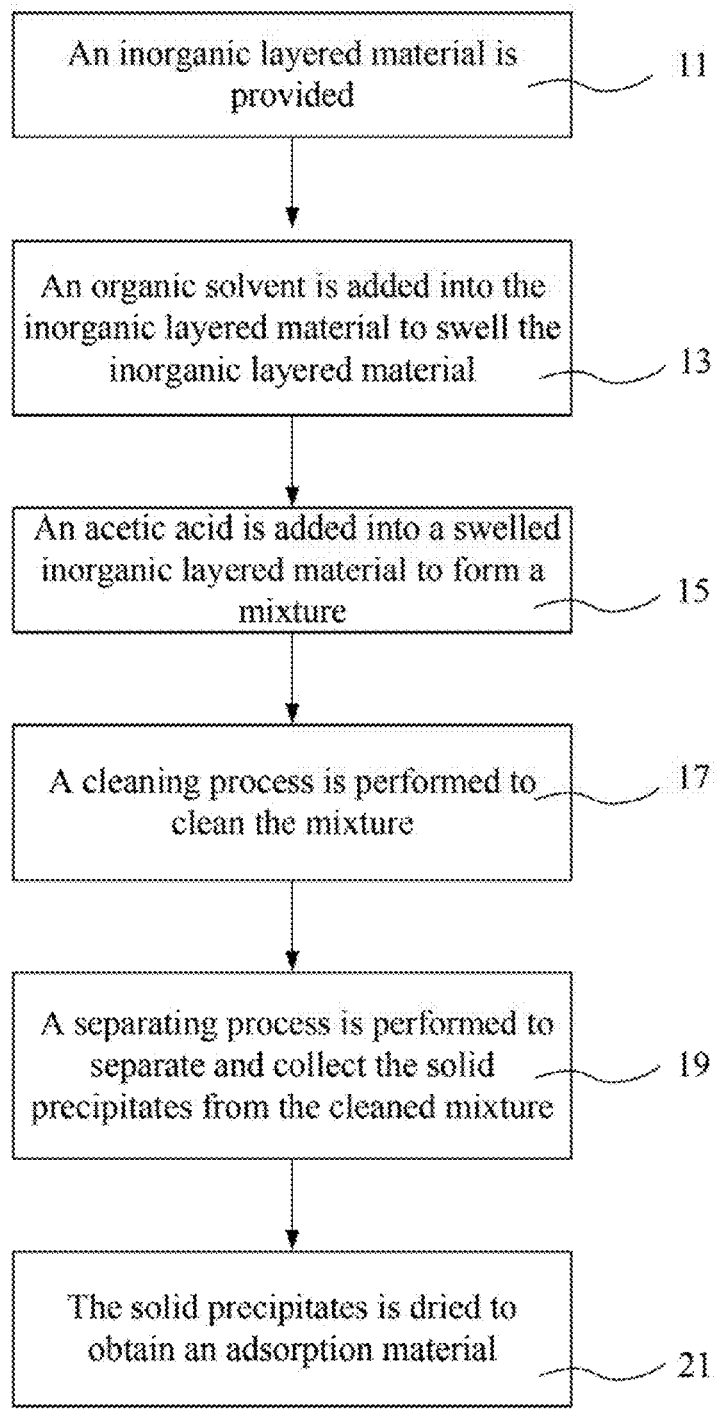
FIG. 1 is a process flow chart showing a method for forming an adsorption material which is used for purifying the protein in accordance with the present invention.

Please refer to FIG. 1. FIG. 1 shows a flow chart of a method for forming an adsorption material which is used for the protein purification. In FIG. 1, the step 11 shows an inorganic layered material that is provided. In step 11, the material of inorganic layered material is layered double hydroxide (LDH) or hydrotacite. In general, the typical layered double hydroxide is constituted by two metal ions. The different type layered double hydroxide can be constituted by the different metal ions and different interlayered anion, $A^{m-}$. For example, Mg—Al—$CO_3$ LDH is constituted by magnesium ions ($Mg^{2+}$), aluminum ion ($Al^{3+}$) and carbonate ions ($CO_3^{2-}$), or Li—Al—Cl LDH is constituted by lithium ion (Lr), aluminum ion ($Al^{3+}$), and chloride ion ($Cl^-$). In an embodiment of the present invention, the inorganic layered material is lithium-aluminum layered double hydroxide, and the anion exchange capacity (AEC) is about 250 meq/100 g.

Then, the step 13 shows an organic solvent that is added into the inorganic layered material to swell the inorganic layered material. In step 13, the added amount of the organic solvent is required to swell the inorganic layered material completely, in which the proportion of the inorganic layered material and the organic solvent is 1:5. In present invention, the organic solvent is formamide, dimethyl formamide or other organic solvent which can also swell the inorganic layered material to obtain the swelling effect.

Then, the step 15 shows an acetic acid solution that is added into the swelled inorganic layered material to form a mixture. In step 15, the mixing proportion of the swelled inorganic layered material and the acetic acid solution is about 0.3:5, in which the concentration of the acetic acid solution is non-diluted glacial acetic acid. In this embodiment, after the acetic acid solution is added, by the temperature of heating is in the range from 70° C. to 90° C. and using the physical stirring process at the same time, such that the acetic acid solution, the organic solvent and the inorganic layered material is mixed to form the mixture, in which the physical stirring process is magnetic stirring.

The step 17 shows a cleaning process, which utilizes the cleaning solvent to clean the mixture. In step 17, the cleaning solvent compatible with the organic solvent in step 13 to clean the mixture, and thus, the mixture is heated at temperature about 40° C. by the way of alcohol solution and is physical stirred at least two hours at the same time, in which the cleaning solvent is alcohol or ethanol solution.

Next, step 19 shows at least one separating process, and the cleaned mixture is separated and the plurality of solid precipitates (solid phase) is to be collected after separating process. In this step 19, at least one separating process is performed to the cleaned mixture to separate the mixture into a solid-liquid phases solution. It is noted to illustrate that the separating process is centrifuge separating process, and the speed for the centrifuge separating process is in the range between 6,000 rpm and 14,000 rpm. In addition, the centrifuge separating process can be performed repeatedly to separate the solid phase from the solid-liquid phases solution completely, and the plurality of solid precipitates can be collected from the solid-liquid phases solution.

Finally, the step 21 is performed to dry the solid precipitate to obtain the product, adsorption material. In step 21, the drying process is heating, concentrating and extracting or freeze-drying process. The plurality of solid precipitates is the adsorption material which is used for purifying the protein aqueous.

Figure 2:
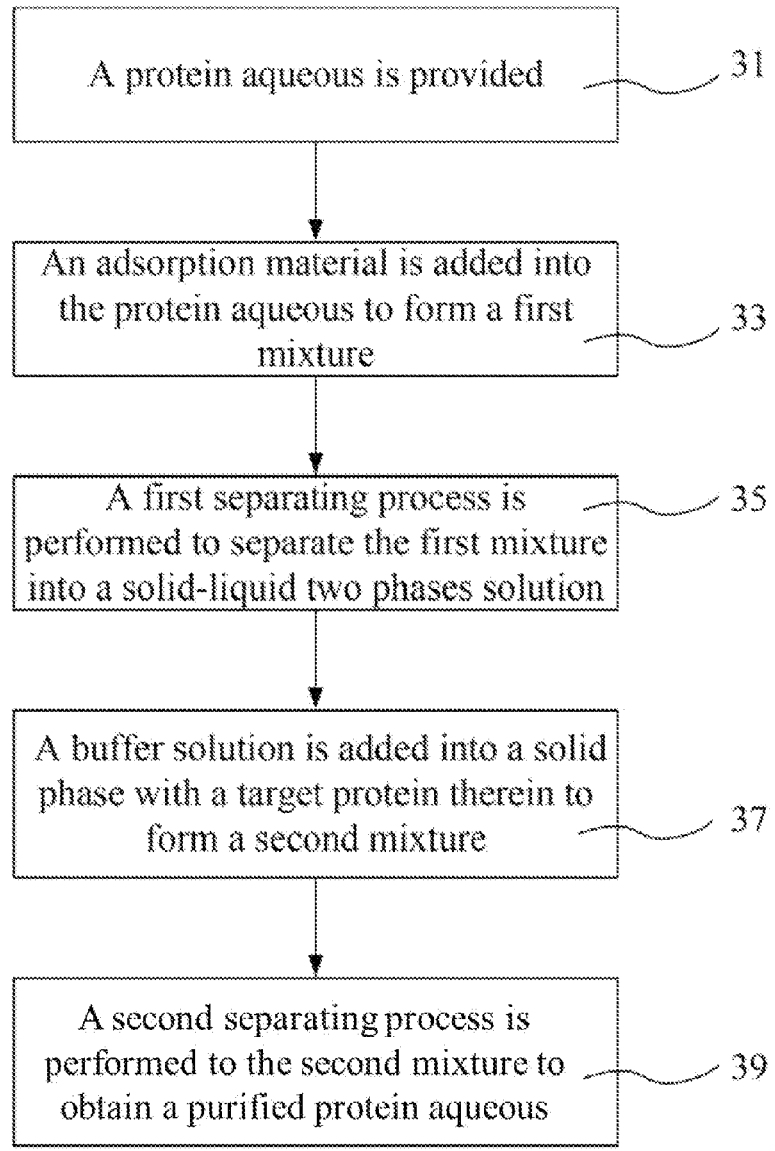
FIG. 2 is a process flow chart showing a method for purifying the protein in accordance with the present invention.

Then, please refer to FIG. 2. FIG. 2 shows a flow chart for a method for purifying the protein aqueous. In FIG. 2, step 31 shows a protein aqueous which is provided. In step 31, the protein aqueous includes Bovina Serum Albumin (BSA) and Lysozyme (LYZ), in which the molecular weight of the BSA is about 68,000 Da, and isoelectric point (PI) is about 4.8, and the molecular weight of LYZ is about 14,300 Da, and PI is about 11.0.

The step 33 shows the adsorption material that is added into the protein aqueous to form a first mixture. In step 33, the adsorption material is formed by above manufacturing processes (step 11 to step 21) which is added into the protein aqueous and is stirred to form the first mixture with solid-liquid two phases solution.

The step 35 shows a first separating process to separate the first mixture into solid-liquid phases two solution. In step 35, the first separating process such as centrifuge separating process, is performed to separate the first mixture into solid-liquid two phases solution respectively; meanwhile, the target protein is stored in the solid phase of the solid-liquid two phases solution.

The step 37 shows the buffer solution which is added into the solid phase of the solid-liquid two phases solution with the target protein to form a second mixture. It should be noted that the buffer solution is an ion exchange solution with strong ion exchange capacity, and the purpose of the buffer solution with strong ion exchange capacity is to achieve the target protein in the protein aqueous. In this embodiment, the buffer solution is phosphate-containing solution, such as phosphate buffer solution, in which the concentration of the buffer solution is about 0.2 mole/liter (M) and the pH value is about 7.0.

Then, the step 39 shows a second separating process to separate the second mixture, so that the purified protein aqueous can be obtained. In step 39, the second mixture is separated into solid-liquid two phases solution, and the liquid phase is extracted from the solid-liquid two phases solution to obtain the purified protein aqueous.

Figure 3:
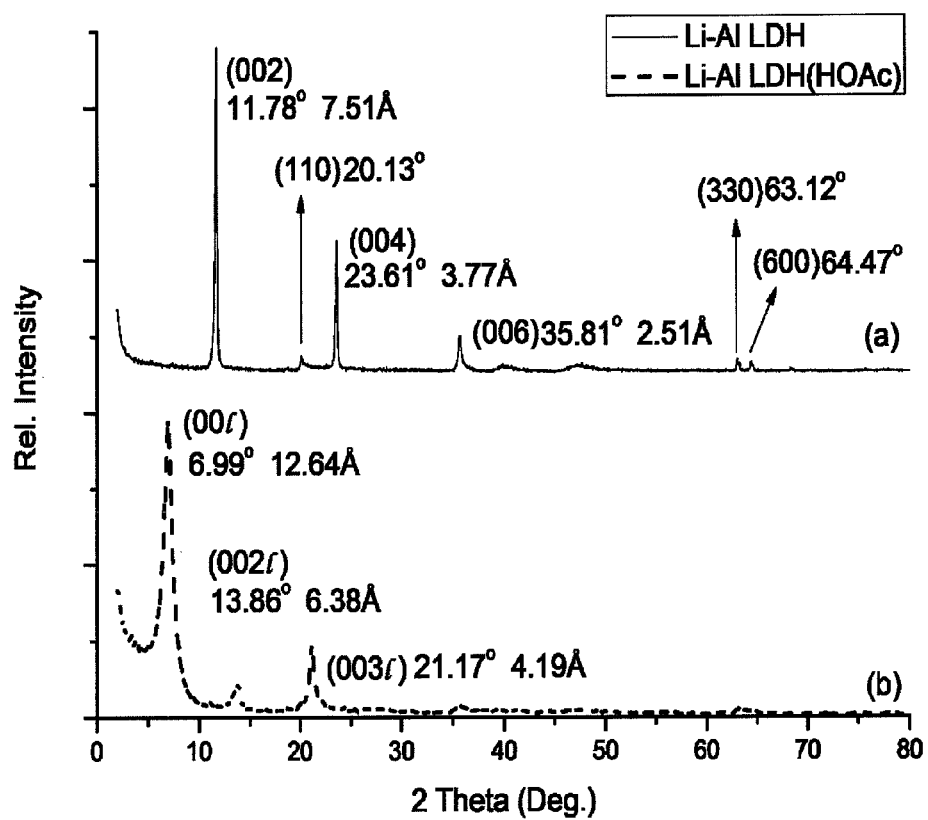
FIG. 3 is a schematic view showing the characteristic peak of an inorganic layered material by using X-ray diffraction analysis in accordance with the present invention.

Next, the present invention utilizes the instrument analysis to prove the adsorption material can purify the protein aqueous effectively. FIG. 3 shows the characteristic peak of an inorganic layered material by using X-ray diffraction analysis. In FIG. 3, the symbol 001 is acetified Li—Al layered double hydroxides with the characteristic peak $2\theta=6.99°$ and d-spacing is 12.64 Å.

Figure 4:
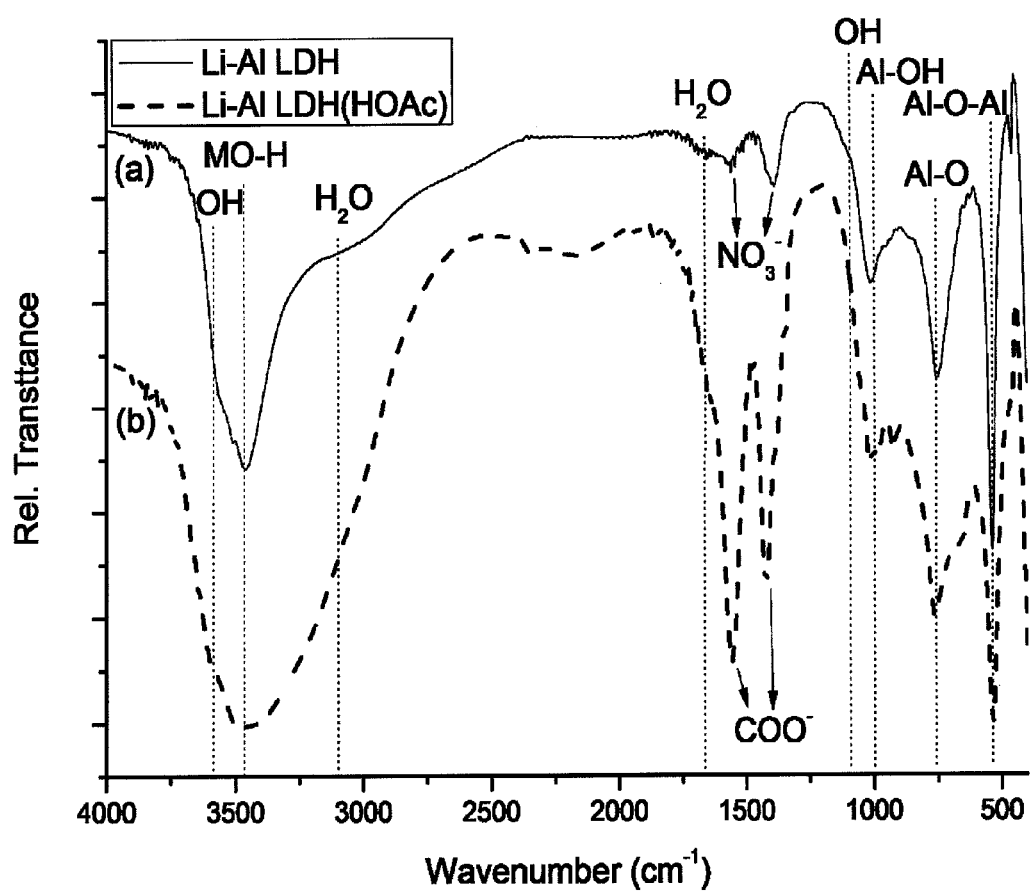
FIG. 4 is a spectrum showing the Fourier Transform Infrared (FT-IR) spectroscopy in accordance with the present invention.

FIG. 4 shows the Fourier Transform Infrared (FT-IR) spectroscopy. In FIG. 4, the acetic acid is successfully connected the surface of Li—Al layered double hydroxides that can be verified, such that the surface of the Li—Al layered double hydroxides with acetic functional group thereon.

Figure 5:
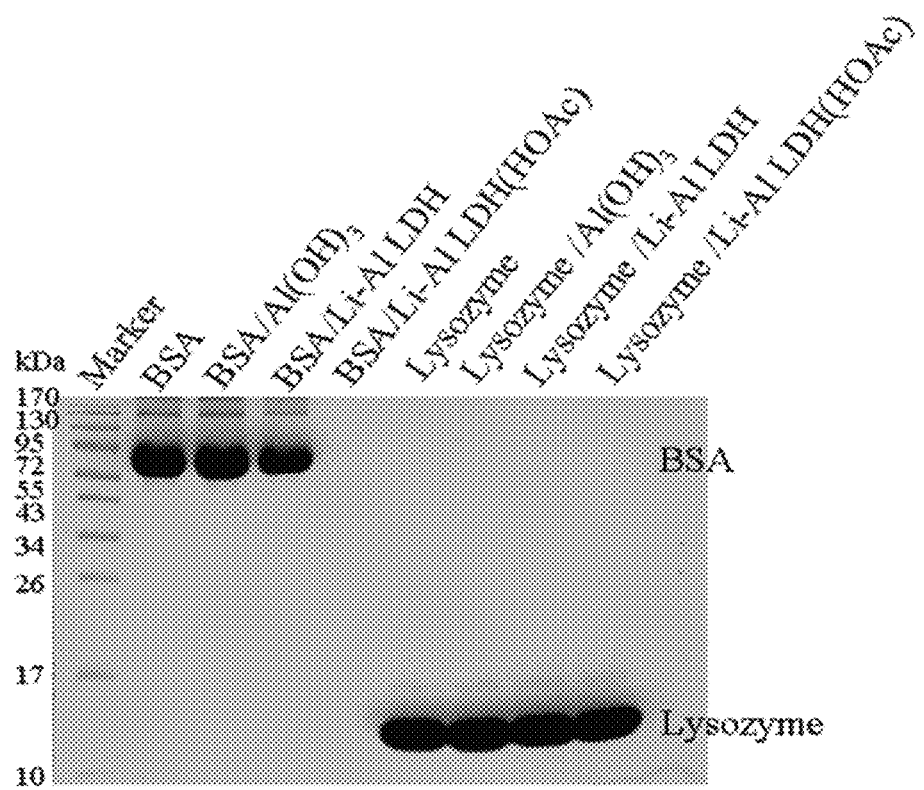
FIG. 5 is an analysis graphic showing sodium dodecyl sulfate polyacrylamide gel electrophoresis (SDS-PAGE) in accordance with the present invention.

FIG. 5 shows an analysis graphic of sodium dodecyl sulfate polyacrylamide gel electrophoresis (SDS-PAGE). The adsorption capacity of acetified Li—Al layered double hydroxides for absorbing the BSA and LYZ is strongly contrast to the conventional Li—Al layered double hydroxides which is not acetified by acetic acid solution. Thus, the acetified Li—Al layered double hydroxide is the key feature to adsorb the protein on the inorganic layered material effectively.

Figure 6:
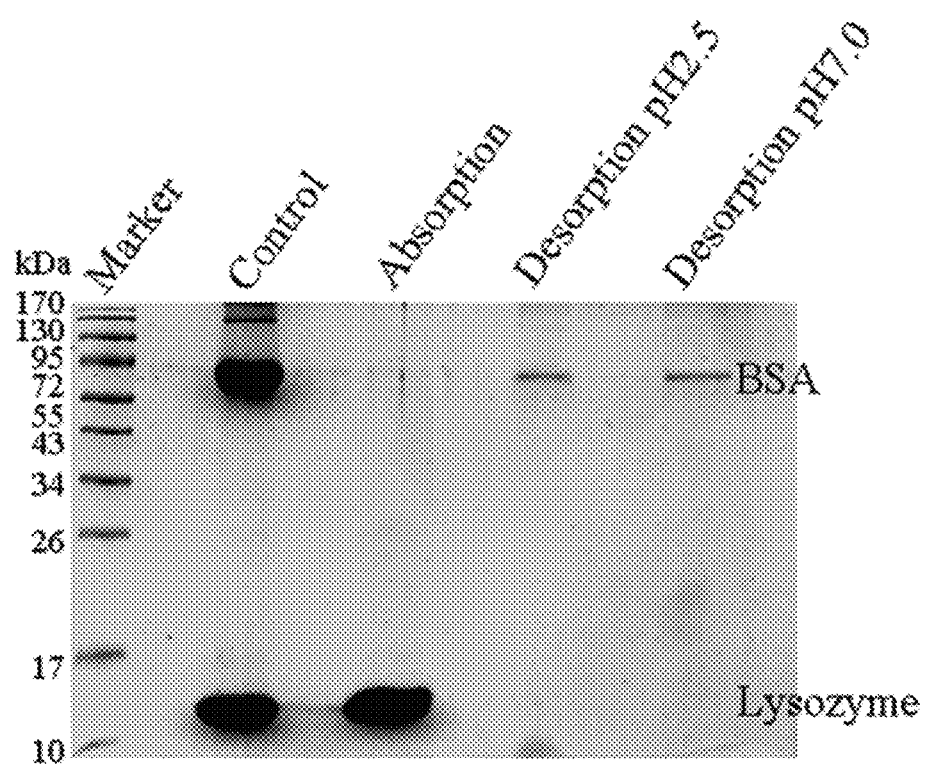
FIG. 6 is another analysis graphic showing sodium dodecyl sulfate polyacrylamide gel electrophoresis (SDS-PAGE) in accordance with the present invention.

FIG. 6 shows another analysis graphic by using sodium dodecyl sulfate polyacrylamide gel electrophoresis (SDS-PAGE). In FIG. 6, when the acetified Li—Al layered double hydroxides is mixed with the protein aqueous with BSA and LYZ, the acetified Li—Al layered double hydroxides shows excellent adsorption ability of BSA that is contrast to LYZ. In addition, the buffer solution with phosphate is utilized to separate BSA from the acetified Li—Al layered double hydroxide, so that the protein can be purified effectively.

According to above discussion, the inorganic layered material used as the adsorption material which can apply for purifying the crude protein aqueous, such that the target protein can be extracted from the crude protein aqueous. By using the purification processes, the purification steps can be reduced and the highly purity of the protein aqueous can also be obtained.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A method to purify a solution containing a target protein by utilizing an acetate inorganic layered material, comprising steps of:
    providing an inorganic layered material;
    adding an organic solvent into the inorganic layered material to swell the inorganic layered material;
    mixing an acetic acid solution with the swelled inorganic layered material to form an acetified mixture containing an acetate inorganic layered material, wherein the acetic acid solution is non-diluted glacial acetic acid;
    performing a cleaning process by using a cleaning solvent to clean the acetified mixture;
    performing at least one centrifuge separating process with the speed between 6,000 rpm and 14,000 rpm to separate the cleaned acetified mixture into a first solid-liquid two phases solution and to collect a plurality of solid phases containing the acetate inorganic layered material from the first solid-liquid phases solution;
    drying the plurality of solid phases to obtain the acetate inorganic layered material;
    providing the solution containing the target protein;
    adding the acetate inorganic layered material into the solution containing the target protein to form a first mixture;
    performing a first separating process to separate the first mixture into a second solid-liquid two phases solution;
    resuspending a solid phase of the second solid-liquid two phases solution by adding an phosphate buffer solution into the solid phase of the second solid-liquid two phases solution to form a second mixture;
    performing a second separating process to separate the second mixture into a third solid-liquid two phases solution; and
    extracting a liquid phase from the third solid-liquid two phases solution to obtain a purified target protein.

2. The method according to claim 1, wherein the inorganic layered material is a material selected from the group consisting of hydrotacite and layered double hydroxides (LDH).

3. The method according to claim 2, wherein the layered double hydroxides (LDH) is Li—Al Layered Double Hydroxides.

4. The method according to claim 1, wherein the proportion of the inorganic layered material to the added organic solvent is 1:5.

5. The method according to claim 1, wherein the organic solvent is selected from the group consisting of formamide and dimethylformamide (DMF).

6. The method according to claim 1, wherein the cleaning solvent is alcohol or acetone.

7. The method according to claim 1, wherein step of drying the plurality of solid phases to obtain the acetate inorganic layered material is performed by a process selected from the group consisting of heating process, extracting and concentrating process, and freeze-drying process.

8. The method according to claim 1, wherein the solution containing the target protein includes Bovine Serum Albumin (BSA) and Lysozyme (LYZ).

9. The method according to claim 1, wherein either the first separating process or the second separating process is centrifuge separating process.

\* \* \* \* \*